United States Patent [19] [11] 4,016,285
Boschetti et al. [45] Apr. 5, 1977

[54] ACETIC ACID DERIVATIVE HAVING CHOLERETIC AND ANTI-INFLAMMATORY ACTIVITY

[75] Inventors: Eugene Boschetti, Venissieux; Philippe Briet; Jean-Jacques Berthelon; Janine Chabert, all of Lyon, all of France

[73] Assignee: Lipha, Lyonnaise Industrielle Pharmaceutique, Lyon, France

[22] Filed: July 28, 1975

[21] Appl. No.: 599,778

[30] Foreign Application Priority Data
Aug. 5, 1974    France ............................ 74.27067

[52] U.S. Cl. .............................................. 424/283
[51] Int. Cl.² ..................................... A61K 31/35
[58] Field of Search ................................. 424/283

[56] References Cited
UNITED STATES PATENTS

| 3,495,009 | 2/1970 | Tronche et al. | 424/283 |
| 3,812,156 | 5/1974 | Bonoca et al. | 260/345.2 |
| 3,864,362 | 2/1975 | Feuer et al. | 260/345.2 |

OTHER PUBLICATIONS

J. Indian Chem. Soc., (1973), 50, 295–298.

Primary Examiner—Frederick E. Waddell
Attorney, Agent, or Firm—Browdy and Neimark

[57] ABSTRACT

The compound α-[6-(2-phenyl)-chromonyl]-acetic acid has choleretic and anti-inflammatory activity and is of use in the treatment of hepatic conditions.

5 Claims, No Drawings

ACETIC ACID DERIVATIVE HAVING CHOLERETIC AND ANTI-INFLAMMATORY ACTIVITY

This invention relates to a pharmacologically active acetic acid derivative and is concerned with its use as a choleretic and anti-inflammatory agent.

The acetic acid derivative which in accordance with the invention has been found to have both choleretic activity and anti-inflammatory activity is the compound α-[6-(2-phenyl)-chromonyl] - acetic acid, which can alternatively be named α-(6-flavonyl)-acetic acid, having the structural formula:

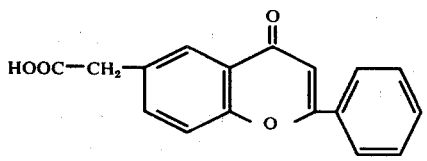

either in the free acid form or in the form of an alkali metal salt thereof, for example the sodium salt.

The compound of formula I is a known compound having been disclosed by S. Patel and S. Sethna in J. Indian Chem. Soc. 1973, 50-295-8. It is an odorless, white solid of bitter taste and with a melting point of 212° C. It is soluble in aqueous alkalis; its alkali metal salts, especially the sodium salt, are soluble in ordinary water; the solutions obtained have an alkaline reaction.

The compound of formula I, either as the free acid or in the form of an alkali metal salt, preferably the sodium salt, will normally be administered in the form of a pharmaceutical composition comprising as an essential pharmacologically active ingredient the compound of formula I, either in free acid or alkali metal salt form, in association with at least one pharmaceutically acceptable carrier or excipient therefor. If desired the composition may be made up in a dosage unit form appropriate to the required mode of administration. Thus for example for oral administration the dosage unit can take the form of a tablet or capsule, for parenteral administration it can take the form of an injectable solution packaged in an ampoule, and for rectal administration it can take the form of a suppository. Each dosage unit may contain from about 100mg. to about 2g. of the active ingredient, whilst the daily dosage may range from about 100mg. to 2g. of the active ingredient.

The choleretic activity of the compound of formula I in free acid form or as an alkali metal salt, particularly the sodium salt, has been established on various species and by different methods.

With the male Wistar rat, by intra-duodenal route, administration of the compound in solution in physiological serum or in propylene glycol, in a dose of 40 mg/kg, produces a considerable and prolonged increase in the biliary excretion.

This choleretic activity is expressed below by the coefficient of PESSON, SALLE AND AUFFRET (Arch. Intern. Pharmacod., 1959, 119, 443), defined as follows, namely:

P. the percentage of animals of which the choleresis is increased by more than 20% (if all the animals have reacted, P = 1).

A. the mean percentage of increase in the choleresis during the test, only the increases higher than 20% being retained.

D. the time, in hours, of this significant increase.

The coefficient P A D is expressed by the product P × A × D.

For the compound of the invention, the P A D is 275; the P A D of sodium dehydrocholate (control) in the standard dose of 50 mg/kg under the same conditions is 88.

These results have been confirmed by tests carried out on adult dogs by the intra-duodenal route at 120 mg/kg and 40 mg/kg. The biliary flow is considerably increased for three hours following the injection.

The anti-inflammatory activity of the compound of formula I is shown by the effect observed in the protection of the erythema from ultra-violet on an albino guinea pig, in the oedema due to carragenine in the rat and in arthritis caused by mycobacterium butyricum in the rat. In these tests, the compound of formula I is shown to be as active in equitoxic doses as the product usually employed as reference compounds (acetylsalicylic acid, phenylbutazone).

The toxicity of the compound of formula I is low. The 50% lethal dose on the mouse is 2400 mg/kg perorally, 350 mg/kg intraperitoneally and 350 mg/kg intravenously.

The compound of formula I can be used for the therapeutic treatment of various hepatic diseases, such as after-effects of jaundice, hepatic congestion, viral hepatitis, and etherosclerosis of plethorics.

An example of a pharmaceutical composition in accordance with the invention is given below:

| | |
|---|---|
| Compound of formula 1 | 200 mg. |
| Corn starch | 60 mg. |
| Talc | 20 mg. |
| Royalgine | 10 mg. |
| Starch | 10 mg. |
| | 300 mg. |

The results of the following actual clinical tests show the efficacy of α-[6-(2-phenyl)-chromonyl]-acetic acid for human therapeutic purposes.

OBSERVATION NO. 1

T, 71 years old, male, a chronic alcoholic affected by a subicterus, anorexia, nauseas and post-prandial flatulence.

Posology and period of treatment: Six 200 mg. tablets per day for 12 days.

Activity: disappearance of the icterus and functional signs. Biological examinations:

| | before treatment | after treatment |
|---|---|---|
| Bilirubinemia mg %. | 10 | 5 |
| MacLagan reaction | + | — |
| Gros reaction | ++ | — |
| Popper reaction | + | — |

Tolerance: Excellent; Conclusion: very good result.

OBSERVATION NO. 2

T, 32 years old, female, dyspeptic syndrome (nauseas, anorexia, apathy of a true hypochondriac, typical migraine) during a vesicular dyskinesia.

Posology and period of treatment: Six 200 mg. tablets per day for 10 days.

Activity: disappearance of the functional symptomatology. Migraines diminished in frequency and intensity. Biological examinations:

|  | before treatment | after treatment |
| --- | --- | --- |
| Bilirubinemia mg %. | 17.5 | 7 |
| MacLagan reaction | + | — |
| Gros reaction | — | — |
| Popper reaction | — | — |

Tolerance: Excellent; Conclusion: very good result.

OBSERVATION NO. 3

S, 27 years old, male, dyspeptic syndrome of vesicular origin (anorexia — nauseas — apathy of true hypochondriac). Posology and period of treatment: Six 200 mg. tablets per day for 20 days.

Activity: very clear improvement in the functional signs.

Tolerance: Excellent; Conclusion: very satisfactory result.

OBSERVATION NO. 4

H, 31 years old, female, biliary dyskinesia. Radiological examination: bladder discharge very considerably slowed down (2 hours).

Posology and period of treatment: Six 200 mg. tablets per day for 10 days.

Activity: very decided improvement. Radiological examination: more rapid bladder discharge.

Tolerance: Perfect; Conclusion: satisfactory result.

OBSERVATION NO. 5

P, 36 years old, male, hyposthenic dyspepsia syndrome with pains orginating from the bladder.

Posology and period of treatment: Six 200 mg. tablets per day for 8 days.

Activity: absolutely complete and very rapid symptomatic improvement.

Tolerance: good; Conclusion: very good result.

OBSERVATION NO. 6

MM, 74 years old, female, biliary dyskinesia (nauseas — vomiting — constipation — sensitivity of a true hypochondriac).

Posology and period of treatment: Six 200 mg. tablets per day for 15 days.

Activity: all the functional signs have disappeared.

Tolerance: very good; Conclusion: excellent result.

It will be appreciated from the foregoing that in accordance with the invention there is provided a method of treating hepatic conditions in humans which comprises administering an effective dose of the compound $\alpha$-[6-(2-phenyl)-chromonyl]-acetic acid or of an alkali metal salt thereof, preferably the sodium salt.

What we claim is:

1. A pharmaceutical composition having choleretic and anti-inflammatory activity, comprising per dosage unit as an essential active ingredient from about 100 mg to about 2 g of $\alpha$-[6-(2-phenyl)-chromonyl]-acetic acid or an alkali metal salt thereof, in association with a pharmaceutically acceptable carrier or excipient therefor.

2. The composition of claim 1, in a dosage unit form suitable for oral administration.

3. The composition of claim 2, wherein the dosage unit is a tablet or capsule.

4. A method of increasing choleretic activity in a patient in need of said therapy, which comprises administering to the patient a therapeutically effective amount of $\alpha$ [6-2(phenyl) chromonyl] acetic acid or of an alkali metal salt thereof.

5. The method of claim 4, wherein said therapy is in the treatment of a condition which is (a) subicterus, (b) vesicular dyskinesia, (c) vesicular dyspepsia, (d) biliary dyskinesia, or (e) hyposthenic dyspepsia.

* * * * *